(12) United States Patent
Chevallier et al.

(10) Patent No.: US 9,022,990 B2
(45) Date of Patent: May 5, 2015

(54) NEEDLE SAFETY SHIELD

(75) Inventors: Stéphane Chevallier, Saint-Soupplets (FR); Jean-Michel Chevallier, Enghien-les-Bains (FR); Hubert Jansen, Stolberg (DE); Alain Feret, Evreux (FR)

(73) Assignee: Tech Group Europe Limited, Dublin (IE)

( * ) Notice: Subject to any disclaimer, the term of this patent is extended or adjusted under 35 U.S.C. 154(b) by 0 days.

(21) Appl. No.: 14/009,814

(22) PCT Filed: Apr. 4, 2011

(86) PCT No.: PCT/US2011/031053
§ 371 (c)(1),
(2), (4) Date: Oct. 25, 2013

(87) PCT Pub. No.: WO2012/138318
PCT Pub. Date: Oct. 11, 2012

(65) Prior Publication Data
US 2014/0163476 A1    Jun. 12, 2014

(51) Int. Cl.
*A61M 5/32* (2006.01)

(52) U.S. Cl.
CPC ....... *A61M 5/326* (2013.01); *A61M 2005/3264* (2013.01)

(58) Field of Classification Search
USPC ......................................................... 604/198
See application file for complete search history.

(56) References Cited

U.S. PATENT DOCUMENTS

| | | | |
|---|---|---|---|
| 1,921,034 A * | 8/1933 | La Marche | 604/157 |
| 3,880,163 A | 4/1975 | Ritterskamp | |
| 4,631,057 A * | 12/1986 | Mitchell | 604/198 |
| 4,723,943 A * | 2/1988 | Spencer | 604/198 |
| 4,747,831 A | 5/1988 | Kulli | |
| 4,828,548 A | 5/1989 | Walter | |

(Continued)

FOREIGN PATENT DOCUMENTS

| EP | 0904792 A2 | 3/1999 |
|---|---|---|
| EP | 0966983 A1 | 12/1999 |

(Continued)

OTHER PUBLICATIONS

Office Action issued Oct. 24, 2013 in U.S. Appl. No. 11/861,567 by Pessin.

(Continued)

*Primary Examiner* — Nicholas Lucchesi
*Assistant Examiner* — Diva K Chander
(74) *Attorney, Agent, or Firm* — Panitch Schwarze Belisario & Nadel LLP (57) ABSTRACT

A needle safety shield 10 for use with a syringe 10 having a barrel 14, a needle and a plunger rod 16. The safety shield 10 has a first tube 22. A second tube 26 is arranged for sliding movement within the first tube 22. A pin 46 is connected to one of the first and second tubes 22, 26. An activation ring 32 has a stop 72. A drive spring 34 biases the activation ring 32 in a proximal direction to place the stop 72 in engagement with the pin 46 to retain the first and second tubes 22, 26 in a retracted configuration. The movement of the plunger rod 16 to engage the activation ring 32 compresses the drive spring 34, moving the activation ring 32 distally, and moving the stop 72 out of engagement with the pin 46, allowing the drive spring 34 to move the first and second tubes 22, 26 into an extended configuration.

15 Claims, 10 Drawing Sheets

(56) References Cited

U.S. PATENT DOCUMENTS

| | | | |
|---|---|---|---|
| 4,832,696 A | 5/1989 | Luther et al. | |
| 4,871,355 A | 10/1989 | Kikkawa | |
| 4,887,998 A | 12/1989 | Martin et al. | |
| 4,911,693 A | 3/1990 | Paris | |
| 4,923,447 A | 5/1990 | Morgan | |
| 4,927,416 A * | 5/1990 | Tomkiel | 604/198 |
| 4,929,237 A * | 5/1990 | Medway | 604/198 |
| 4,931,040 A | 6/1990 | Haber et al. | |
| 4,943,282 A | 7/1990 | Page et al. | |
| 4,966,592 A | 10/1990 | Burns et al. | |
| 4,986,819 A | 1/1991 | Sobel | |
| 5,026,349 A | 6/1991 | Schmitz et al. | |
| 5,106,379 A * | 4/1992 | Leap | 604/198 |
| 5,108,378 A | 4/1992 | Firth et al. | |
| 5,112,307 A | 5/1992 | Haber et al. | |
| 5,141,500 A | 8/1992 | Hake | |
| 5,163,918 A | 11/1992 | Righi et al. | |
| 5,201,708 A | 4/1993 | Martin | |
| 5,201,720 A | 4/1993 | Borgia et al. | |
| 5,261,880 A | 11/1993 | Streck et al. | |
| 5,267,972 A | 12/1993 | Anderson | |
| 5,279,581 A | 1/1994 | Firth et al. | |
| 5,346,480 A | 9/1994 | Hess et al. | |
| 5,360,410 A | 11/1994 | Wacks | |
| 5,380,296 A | 1/1995 | Smedley et al. | |
| 5,411,487 A | 5/1995 | Castagna | |
| 5,501,672 A | 3/1996 | Firth et al. | |
| 5,531,706 A | 7/1996 | de la Fuente | |
| 5,558,651 A | 9/1996 | Crawford et al. | |
| 5,573,513 A | 11/1996 | Wozencroft | |
| 5,591,138 A | 1/1997 | Vaillancourt | |
| 5,601,536 A | 2/1997 | Crawford et al. | |
| 5,803,918 A | 9/1998 | Vetter et al. | |
| 5,817,064 A | 10/1998 | DeMarco et al. | |
| 5,855,839 A * | 1/1999 | Brunel | 264/524 |
| 5,891,104 A | 4/1999 | Shonfeld et al. | |
| 5,891,105 A | 4/1999 | Mahurkar | |
| 5,913,846 A | 6/1999 | Szabo | |
| 5,989,226 A | 11/1999 | Hymanson | |
| 5,997,513 A | 12/1999 | Smith et al. | |
| 6,013,059 A | 1/2000 | Jacobs | |
| 6,033,386 A | 3/2000 | Novacek et al. | |
| 6,086,566 A | 7/2000 | Arnissolle | |
| 6,159,184 A | 12/2000 | Perez et al. | |
| 6,171,284 B1 | 1/2001 | Kao et al. | |
| 6,186,980 B1 | 2/2001 | Brunel | |
| 6,296,625 B1 | 10/2001 | Vetter et al. | |
| 6,319,233 B1 | 11/2001 | Jansen et al. | |
| 6,319,234 B1 | 11/2001 | Restelli et al. | |
| 6,344,032 B1 | 2/2002 | Perez et al. | |
| 6,416,323 B1 | 7/2002 | Grenfell et al. | |
| 6,419,658 B1 | 7/2002 | Restelli et al. | |
| 6,475,194 B2 | 11/2002 | Domici, Jr. et al. | |
| 6,547,764 B2 | 4/2003 | Larsen et al. | |
| 6,565,540 B1 | 5/2003 | Perouse et al. | |
| 6,569,115 B1 * | 5/2003 | Barker et al. | 604/110 |
| 6,585,702 B1 | 7/2003 | Brunel | |
| 6,613,022 B1 | 9/2003 | Doyle | |
| 6,623,459 B1 | 9/2003 | Doyle | |
| 6,685,676 B2 | 2/2004 | Jansen et al. | |
| 6,719,730 B2 * | 4/2004 | Jansen et al. | 604/192 |
| 6,918,889 B1 | 7/2005 | Brunel | |
| 6,949,086 B2 | 9/2005 | Ferguson et al. | |
| 6,966,898 B1 * | 11/2005 | Pouget et al. | 604/197 |
| 6,997,901 B2 | 2/2006 | Popovsky | |
| 7,029,461 B2 | 4/2006 | Ferguson et al. | |
| 7,097,636 B2 | 8/2006 | Pessin | |
| 7,144,389 B2 | 12/2006 | Ferguson et al. | |
| 7,300,421 B1 | 11/2007 | Lowry et al. | |
| 7,429,256 B2 | 9/2008 | Chevallier et al. | |
| 7,582,073 B2 * | 9/2009 | Barrelle et al. | 604/192 |
| 7,678,086 B2 | 3/2010 | Chevallier | |
| 7,699,814 B2 * | 4/2010 | Lande | 604/198 |
| 7,824,379 B2 * | 11/2010 | Doyle | 604/198 |
| 7,875,006 B2 | 1/2011 | Pessin | |
| 7,938,808 B2 | 5/2011 | Pessin | |
| 8,118,787 B2 | 2/2012 | Chevallier et al. | |
| 8,192,407 B2 | 6/2012 | Pessin | |
| 2001/0031949 A1 | 10/2001 | Asbaghi | |
| 2001/0039401 A1 | 11/2001 | Ferguson et al. | |
| 2002/0002354 A1 | 1/2002 | Vetter et al. | |
| 2002/0045864 A1 | 4/2002 | Perez et al. | |
| 2002/0068921 A1 | 6/2002 | McWethy et al. | |
| 2002/0156426 A1 | 10/2002 | Gagnieux et al. | |
| 2002/0161337 A1 | 10/2002 | Shaw et al. | |
| 2002/0193746 A1 | 12/2002 | Chevallier | |
| 2003/0050607 A1 | 3/2003 | Gagnieux et al. | |
| 2003/0229314 A1 | 12/2003 | McWethy et al. | |
| 2004/0015137 A1 | 1/2004 | Hohlfelder et al. | |
| 2004/0144668 A1 | 7/2004 | Marshall et al. | |
| 2004/0193120 A1 | 9/2004 | Ferguson et al. | |
| 2004/0236283 A1 | 11/2004 | Tang | |
| 2004/0267206 A1 | 12/2004 | Rimlinger et al. | |
| 2005/0020985 A1 | 1/2005 | Doyle | |
| 2005/0080383 A1 | 4/2005 | Woehr | |
| 2005/0119623 A1 | 6/2005 | Pessin | |
| 2005/0148933 A1 | 7/2005 | Raven et al. | |
| 2005/0148943 A1 | 7/2005 | Chevalier | |
| 2005/0165353 A1 | 7/2005 | Pessin | |
| 2006/0184133 A1 | 8/2006 | Pessin | |
| 2006/0200077 A1 | 9/2006 | Righi et al. | |
| 2006/0264887 A1 * | 11/2006 | Lande | 604/500 |
| 2007/0088287 A1 | 4/2007 | Chevallier | |
| 2007/0179441 A1 | 8/2007 | Chevallier | |
| 2007/0239117 A1 | 10/2007 | Chelak et al. | |
| 2008/0021409 A1 | 1/2008 | Pessin | |
| 2008/0208140 A1 | 8/2008 | Barrelle | |
| 2008/0294120 A1 | 11/2008 | Chevallier et al. | |
| 2008/0312603 A1 | 12/2008 | Chevallier et al. | |
| 2009/0105661 A1 | 4/2009 | Chevallier et al. | |
| 2010/0217205 A1 | 8/2010 | Chevallier et al. | |
| 2012/0022465 A1 * | 1/2012 | Stamp et al. | 604/198 |
| 2012/0095408 A1 | 4/2012 | Eaton et al. | |

FOREIGN PATENT DOCUMENTS

| | | |
|---|---|---|
| EP | 1 066 848 A2 | 1/2001 |
| EP | 1474194 A1 | 11/2004 |
| EP | 1532997 A1 | 5/2005 |
| EP | 1235603 B1 | 5/2006 |
| FR | 2653667 A1 | 5/1991 |
| FR | 2762790 A1 | 11/1998 |
| FR | 2794650 A1 | 12/2000 |
| FR | 2807665 A1 | 10/2001 |
| FR | 2830764 A1 | 4/2003 |
| FR | 2830765 A1 | 4/2003 |
| FR | 2835753 A1 | 8/2003 |
| FR | 2837107 A1 | 9/2003 |
| FR | 2860162 A1 | 4/2005 |
| FR | 2861598 A1 | 5/2005 |
| FR | 2922455 A1 | 4/2009 |
| JP | H05-500621 T | 2/1993 |
| JP | H08-010324 A | 1/1996 |
| JP | H09-502893 T | 3/1997 |
| JP | 2843677 B2 | 1/1999 |
| JP | H11-319090 A | 11/1999 |
| JP | 2003-501218 A | 1/2003 |
| JP | 2003-511106 A | 3/2003 |
| JP | 2004-528075 T | 9/2004 |
| JP | 2005-516741 T | 6/2005 |
| JP | 2006-505340 A | 2/2006 |
| WO | 9426334 A1 | 11/1994 |
| WO | 9835714 A1 | 8/1998 |
| WO | 99 17823 A1 | 4/1999 |
| WO | 0124856 A1 | 4/2001 |
| WO | 0130427 A1 | 5/2001 |
| WO | 0137898 A2 | 5/2001 |
| WO | 0141841 A2 | 6/2001 |
| WO | 0185239 A2 | 11/2001 |
| WO | 02072182 A1 | 9/2002 |
| WO | 02089878 A1 | 11/2002 |
| WO | 03068298 A1 | 8/2003 |
| WO | 03/077977 A2 | 9/2003 |
| WO | 2004043524 A1 | 5/2004 |

(56) References Cited

FOREIGN PATENT DOCUMENTS

| WO | 2004087242 A1 | 10/2004 |
|---|---|---|
| WO | 2005039678 A2 | 5/2005 |
| WO | 2006/027445 A1 | 3/2006 |

OTHER PUBLICATIONS

Int'l Search Report issued Dec. 12, 2012 in Int'l Application PCT/US2012/039385.
Int'l Search Report and Written Opinion issued Dec. 22, 2011 in Int'l Application PCT/US2011/031053.
Office Action issued Mar. 28, 2007 in U.S. Appl. No. 10/550,524.
Int'l Search Report issued Sep. 22, 2004 in Int'l Application No. PCT/FR2004/000755.
Office Action issued Apr. 17, 2009 in U.S. Appl. No. 11/861,567.
Office Action issued Jan. 13, 2010 in U.S. Appl. No. 11/861,567.
Office Action issued Sep. 1, 2009 in JP Application No. 2006-505752.
Office Action issued Jun. 8, 2010 in JP Application No. 2006-505752.
Office Action issued Dec. 7, 2010 in JP Application No. 2006-505752.
Japanese Office Action mailed Mar. 16, 2010 in JP Appln No. 2006-537346.
Search Report Issued Jul. 9, 2009 in EP Application No. 08 166 632.3.
Search Report Issued Jun. 13, 2008 in FR Application No. 0758496.
Office Action issued Mar. 22, 2011 in U.S. Appl. No. 12/738,509.
Office Action issued Aug. 25, 2011 in U.S. Appl. No. 12/738,509.
Int'l Search Report issued May 11, 2009 in Int'l Application No. PCT/FR2008/051908; Written Opinion.
Search Report issued Jun. 17, 2008 in FR Application No. 0758497; Written Opinion.
Office Action issued Dec. 23, 2011 in CN Application No. 200880112730.3.
Japanese Office Action mailed Feb. 2, 2010 in Japanese Appln No. 2006-536115.
Office Action Issued Oct. 2, 2008 in U.S. Appl. No. 10/576,938.
Office Action Issued Jul. 21, 2009 in U.S. Appl. No. 10/576,938.
Preliminary Search Report Issued Jun. 21, 2004 in FR Application No. 0312327.
International Search Report and Written Opinion mailed Jun. 6, 2005 in Int'l Application No. PCT/FR2004/002654.
Office Action Issued Dec. 22, 2008 in EP Application No. 04817285.2.
Int'l Preliminary Report on Patentability Issued Jul. 27, 2006 in Int'l Application No. PCT/FR2004/002654.
Office Action dated Mar. 9, 2010 in U.S. Appl. No. 10/576,938.
Office Action issued Sep. 14, 2010 in Japanese Appl Ser No. 2006-536115.
Int'l Preliminary Report on Patentability issued Oct. 8, 2013 in Int'l Application No. PCT/US2011/031053.
Office Action issued Dec. 18, 2006 in U.S. Appl. No. 10/507,913 by Pessin.
Office Action issued Sep. 7, 2007 in U.S. Appl. No. 10/507,913 by Pessin.
Office Action issued Dec. 17, 2008 in U.S. Appl. No. 10/507,913 by Pessin.
Office Action issued Oct. 8, 2009 in U.S. Appl. No. 10/507,913 by Pessin.
Office Action issued Apr. 23, 2009 in EP Application No. 04 818 444.4.
Office Action issued Nov. 23, 2010 in EP Application No. 04 818 444.4.
Office Action issued Apr. 17, 2013 in EP Application No. 04 818 444.4.
Int'l Search Report issued Sep. 11, 2003 in Int'l Application No. PCT/FR2003/000722.
Search Report and English translation of Written Opinion issued Jul. 9, 2009 in EP Application No. 08 166 632.3.
Office Action issued Apr. 21, 2005 in U.S. Appl. No. 10/995,035 by Pessin.
Office Action issued Oct. 5, 2005 in U.S. Appl. No. 10/995,035 by Pessin.
Office Action issued Sep. 28, 2010 in JP Application No. 2007-528915.
Office Action issued Sep. 6, 2011 in JP Application No. 2007-528915.
Int'l Search Report issued Jan. 3, 2006 in Int'l Application No. PCT/FR2005/001983.
Int'l Preliminary Report on Patentability issued Feb. 28, 2007 in Int'l Application No. PCT/FR2005/01983.
Int'l Search Report issued Jan. 25, 2006 in Int'l Application No. PCT/FR2005/001926.
Int'l Preliminary Report on Patentability issued Feb. 28, 2007 in Int'l Application No. PCT/FR2005/001926.
Office Action issued May 15, 2009 in U.S. Appl. No. 11/574,333 by Pessin.
Office Action issued Sep. 10, 2008 in U.S. Appl. No. 11/574,333 by Pessin.
Office Action issued Dec. 13, 2007 in U.S. Appl. No. 11/574,333 by Pessin.
Office Action issued Aug. 20, 2010 in U.S. Appl. No. 11/574,176 by Pessin.
Int'l Preliminary Report on Patentability issued Feb. 21, 2006 in Int'l Application No. PCT/FR2004/000755.
Search Report issued Mar. 4, 2004 in FR Application No. 0312642.
Int'l Search Report issued Apr. 4, 2005 in Int'l Application No. PCT/FR2004/002597.
Int'l Preliminary Report on Patentability issued Dec. 12, 2013 in Int'l Application No. PCT/US2012/039385.
Office Action issued Mar. 11, 2009 in U.S. Appl. No. 10/577,380 by Chevallier.
Office Action issued Feb. 16, 2012 in CN Application No. 200880112413.1.
Search Report and Written Opinion issued Jun. 13, 2008 in FR Application No. 0758495.
Int'l Search Report and Written Opinion issued May 11, 2009 in Int'l Application No. PCT/FR2008/051907.
Int'l Preliminary Report on Patentability issued Jun. 1, 2010 in Int'l Application No. PCT/FR2008/051907.
Office Action issued Mar. 22, 2011 in U.S. Appl. No. 12/738,422.
Office Action issued Aug. 18, 2011 in U.S. Appl. No. 12/738,422.
Office Action issued Jul. 1, 2009 in U.S. Appl. No. 12/254,266 by Chevallier.
Office Action issued Feb. 4, 2010 in U.S. Appl. No. 12/254,266 by Chevallier.
Office Action issued Nov. 3, 2011 in U.S. Appl. No. 12/254,266 by Chevallier.
Office Action issued Apr. 23, 2012 in U.S. Appl. No. 12/254,266 by Chevallier.
Office Action issued May 10, 2013 in U.S. Appl. No. 12/254,266 by Chevallier.
Office Action issued Oct. 10, 2013 in U.S. Appl. No. 12/254,266 by Chevallier.
U.S. Appl. No. 13/666,588 by Feret, filed Nov. 1, 2012.
Int'l Preliminary Report on Patentability issued Jun. 1, 2010 in Int'l Application No. PCT/FR2008/051908.
Search Report issued Jun. 24, 2004 in FR Application No. 0312327.
Office Action issued Sep. 28, 2010 in JP Application No. 2007-528913.
Search Report issued Feb. 22, 2005 in EP Application No. 04 29 2750.
Office Action issued Nov. 28, 2006 in EP Application No. 04 292 750.
Office Action issued Mar. 11, 2008 in EP Application No. 04 292 750.
Office Action issued Sep. 11, 2009 in EP Application No. 05 792 448.
Int'l Preliminary Report on Patentability issued Oct. 17, 2013 in Int'l Application No. PCT/US2011/031053.
Office Action issued Jun. 16, 2014 in U.S. Appl. No. 10/576,938 by Chevalier.
Office Action issued Jun. 24, 2014 in U.S. Appl. No. 12/738,509 by Chevalier.
Office Action issued Dec. 3, 2014 in U.S. Appl. No. 12/738,509 by Chevalier.
Office Action issued Jan. 8, 2015 in U.S. Appl. No. 10/576,938 by Chevalier.

* cited by examiner

NEEDLE SAFETY SHIELD

CROSS-REFERENCE TO RELATED APPLICATION

This application is a section 371 of International Application No. PCT/US2011/031053, filed Apr. 4, 2011, which was published in the English language on Oct. 11, 2012 under International Publication No. WO 2012/138318, the disclosure of which is incorporated herein by reference.

BACKGROUND OF THE INVENTION

The present invention is directed to a needle safety shield for a syringe having a barrel, a needle and a plunger rod. More, particularly, the present invention is directed to a needle safety shield having a position biased actuation assembly.

Needlestick injuries are a well known occupational hazard for healthcare workers. Unintended needlesticks have the potential for transmitting blood-borne viruses such as hepatitis B and C and the human immunodeficiency virus (HIV) to the recipient. After a needlestick injury, certain procedures must be followed to minimize the risk of infection for the recipient, such as laboratory blood tests and post-exposure prophylaxis started immediately after exposure to a pathogen, such as one of the aforementioned viruses, in order to prevent infection by the pathogen and the development of the associated disease.

Conventional safety devices intended to reduce the frequency of post-injection needlesticks typically have a sheath partially or completely surrounding the pharmaceutical syringe. The sheath may be held in a retracted position exposing the needle for aspiration and injection and may be automatically deployed around a needle afterwards.

One example of a common safety injection device for a syringe is disclosed in U.S. Pat. No. 7,678,086. The disclosed safety injection device has a support sheath secured to a syringe barrel. Prior to an injection, a needlestick protection sheath is held in a retracted position exposing the syringe needle by radially outwardly biased latches that rest on a shoulder of the interior wall of the support sheath. At the end of the injection, the head of the syringe piston dislodges the latches allowing a thrust spring to move the protection sheath to an extended position beyond the distal end of the needle, thereby preventing exposure of a healthcare worker to the needle tip. At least one known deficiency of the safety injection device is that a shock or vibration prior to assembly of the syringe may unexpectedly cause the latches to release and the protection sheath to move to the extended position.

Accordingly, there is a need in the art for a safety injection device having a protection sheath that can not be inadvertently activated.

BRIEF SUMMARY OF THE INVENTION

Briefly stated, one aspect of the invention is directed to a needle safety shield for a pharmaceutical syringe having a barrel with a proximal end and a distal end, a piston rod having a distal end slideably received in the barrel, a free proximal end of the piston rod having an actuator head with a rim. The safety shield comprises an outer tube having the syringe barrel therein. A proximal end of the outer tube forms a coupling ring connecting the proximal end of the syringe barrel to the outer tube. The coupling ring is configured to receive the rim of the actuator head therein. The coupling ring has a radially inwardly-extending support. An activation ring is slideably received in the coupling ring. The activation ring comprises a radially inwardly-extending stop movable relative to the support. An inner tube is in an annular space formed between the syringe barrel and the outer tube. An inner-tube pin extends radially outwardly from a proximal end of the inner tube. The inner tube is slideable between a retracted position in which the inner-tube pin is releasably retained on the support by the stop and an extended position in which the inner-tube pin is released by the stop and the inner tube projects beyond the distal end of the syringe barrel. A thrust spring has a proximal end bearing against the activation ring and a distal end bearing against the inner tube. A compressive force is applied to the actuation ring by the thrust spring when the inner tube is in the retracted position. The thrust spring moves the inner tube from the retracted position to the extended position when the rim of the actuator head displaces the activation ring releasing the inner-tube pin from the actuation-ring stop.

Another aspect of the invention is a needle safety shield for a pharmaceutical syringe having a barrel with a proximal end and a distal end, a piston rod having a distal end slideably received in the barrel, a free proximal end of the piston rod having an actuator head with a rim. The safety shield comprises an outer tube having the syringe barrel therein. A proximal end of the outer tube forms a coupling ring connecting the proximal end of the syringe barrel to the outer tube. The coupling ring is configured to receive the rim of the actuator head therein. The coupling ring has a radially inwardly-extending support with an inclined surface. An activation ring is slideably received in the coupling ring. The activation ring comprises a radially inwardly-extending stop movable axially relative to the support. An inner tube is in an annular space formed between the syringe barrel and the outer tube. An inner-tube pin extends radially outwardly from a proximal end of the inner tube. The inner tube is slideable between a retracted position in which the inner-tube pin is releasably retained on the inclined surface of the support by the stop and an extended position in which the inner-tube pin is released by the stop and the inner tube projects beyond the distal end of the syringe barrel. A thrust spring is in the inner tube. The thrust spring has a proximal end bearing against the activation ring and a distal end bearing against the inner tube. A compressive force is applied to the actuation ring by the thrust spring when the inner tube is in the retracted position. The thrust spring moves the inner tube from the retracted position to the extended position when the rim of the actuator head displaces the activation ring releasing the inner-tube pin from the actuation-ring stop.

Another aspect of the invention is a needle safety shield for use with a syringe having a barrel, a needle and a plunger rod. The safety shield has a first tube. A second tube is arranged for sliding movement within the first tube. A pin is connected to one of the first and second tubes. An activation ring has a stop. A drive spring biases the activation ring in a proximal direction to place the stop in engagement with the pin to retain the first and second tubes in a retracted configuration. The movement of the plunger rod to engage the activation ring compresses the drive spring, moving the activation ring distally, and moving the stop out of engagement with the pin, allowing the drive spring to move the first and second tubes into an extended configuration.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings.

DETAILED DESCRIPTION OF THE INVENTION

Reference will now be made in detail to embodiments of the invention, examples of which are illustrated in the accompanying drawings. The terminology used in the description of the invention herein is for the purpose of describing particular embodiments only and is not intended to be limiting of the invention.

As used in the description of the invention and the appended claims, the singular forms "a", "an" and "the" are intended to include the plural forms as well, unless the context clearly indicates otherwise. The words "and/or" as used herein refers to and encompasses any and all possible combinations of one or more of the associated listed items. The words "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The words "right," "left," "lower" and "upper" designate directions in the drawings to which reference is made. The words "inwardly" and "outwardly" refer to directions toward and away from, respectively, the geometric center of the needle safety shield, and designated parts thereof. The terminology includes the words noted above, derivatives thereof and words of similar import.

Although the words first, second, etc., are used herein to describe various elements, these elements should not be limited by these words. These words are only used to distinguish one element from another. For example, a first tube could be termed a second tube, and, similarly, a second tube could be termed a first tube, without departing from the scope of the present invention.

As used herein, the words "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The following description is directed towards various embodiments of a needle safety shield in accordance with the present invention.

Referring to the drawings in detail, where like numerals indicate like elements throughout, there is shown in FIGS. 1-10C a preferred embodiment of the needle safety shield, generally designated 10, and hereinafter referred to as the "safety shield" 10 in accordance with the present invention. The safety shield 10 is for use with a syringe 12. The syringe 12 is preferably a pharmaceutical syringe. However, the syringe 12 may have non-pharmaceutical uses in industry and/or the home. The syringe 12 has a barrel 14 with a proximal end 14a and a distal end 14b. In some embodiments, a needle 13 may be attached fixedly or removably to the distal end 14b of the barrel 14. A piston (or plunger) rod 16 is movable in the barrel 14. In some embodiments, a free proximal end 16a of the piston rod 16 has an actuator head 18 with a rim 20 and a distal end 16b of the piston rod 16 is slideably received in the barrel 14.

The safety shield 10 comprises at least a first (or outer) tube 22 having the syringe 12 therein. In some embodiments, a coupling ring 24 having a support 66 (see FIG. 7) is connected to the first tube 22. Preferably, the proximal end 22a (see FIG. 3) of the outer tube 22 and the coupling ring 24 are formed as a single part connecting the proximal end 14a of the syringe barrel 14 to the outer tube 22. In some embodiments, the outer tube 22 and the coupling ring 24 may be fabricated as separate parts that are subsequently assembled as a single part by a joining process such as ultrasonic welding.

A second (or inner) tube 26 is in the first tube 22. The second tube 26 is arranged for sliding movement within the first tube 22. Preferably, the second tube 26 is in an annular space 28 formed between the syringe barrel 14 and the outer tube 22. A pin 46 (see FIG. 5) is connected to one of the first and second tubes 22, 26. In some embodiments, the pin 46 is preferably connected to the second tube 26.

An activation ring 32 having a stop 72 is provided. (See FIG. 8) In some embodiments, the activation ring 32 may be slideably received in the coupling ring 24.

A drive (or thrust) spring 34 biases the activation ring 32 in a proximal direction to place the stop 72 in engagement with the pin 46 to retain the first and second tubes 22, 26 in a retracted configuration. In some embodiments, when the safety shield 10 is in the retracted configuration the support 66 and stop 72 form a pocket (or latch) 48 in which the pin 46 is received. (See FIGS. 10A-10C). Preferably, the pocket 48 is formed by an inclined surface 70 on the support 66 extending radially and at an angle to the axis 36 of the first and second tubes 22, 26 and a first surface 74 on the stop 72 extending radially and parallel to the axis 36.

Figure 1:
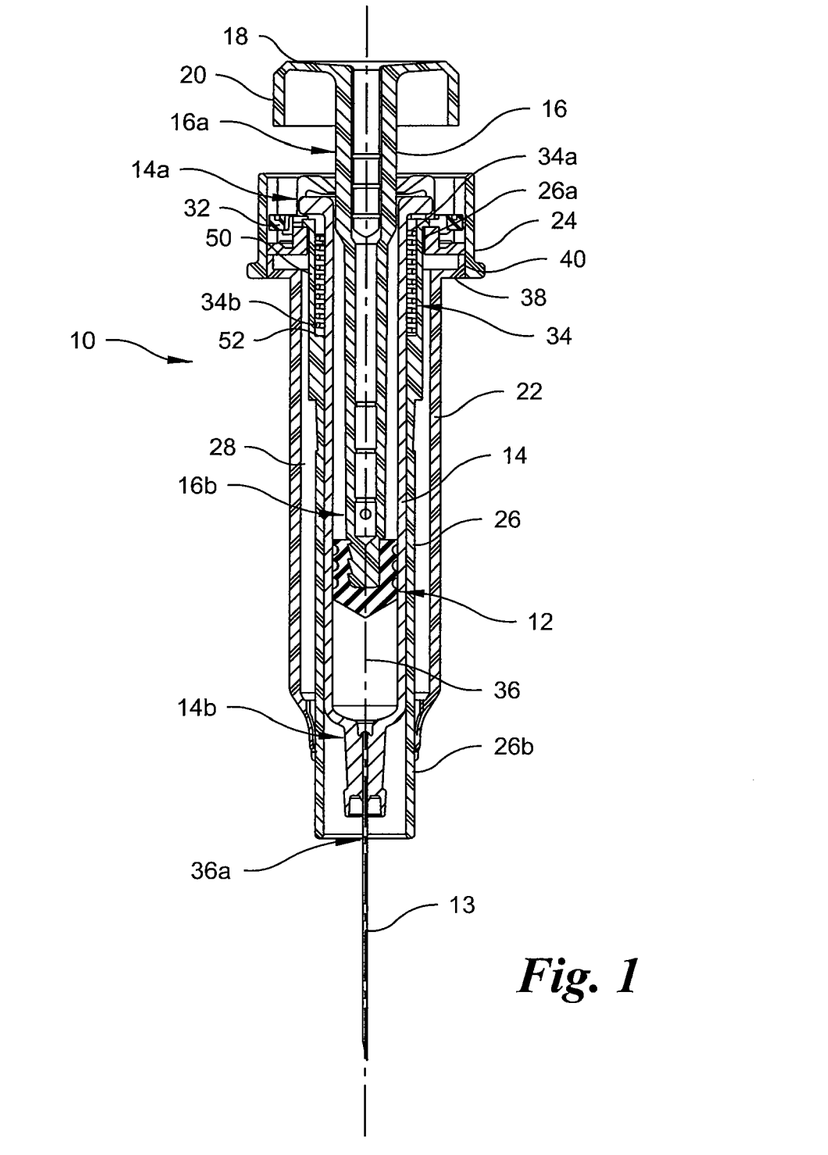
FIG. 1 is a side cross-sectional view of an embodiment of the needle safety shield containing a pharmaceutical syringe in accordance with the present invention.
Figure 2:
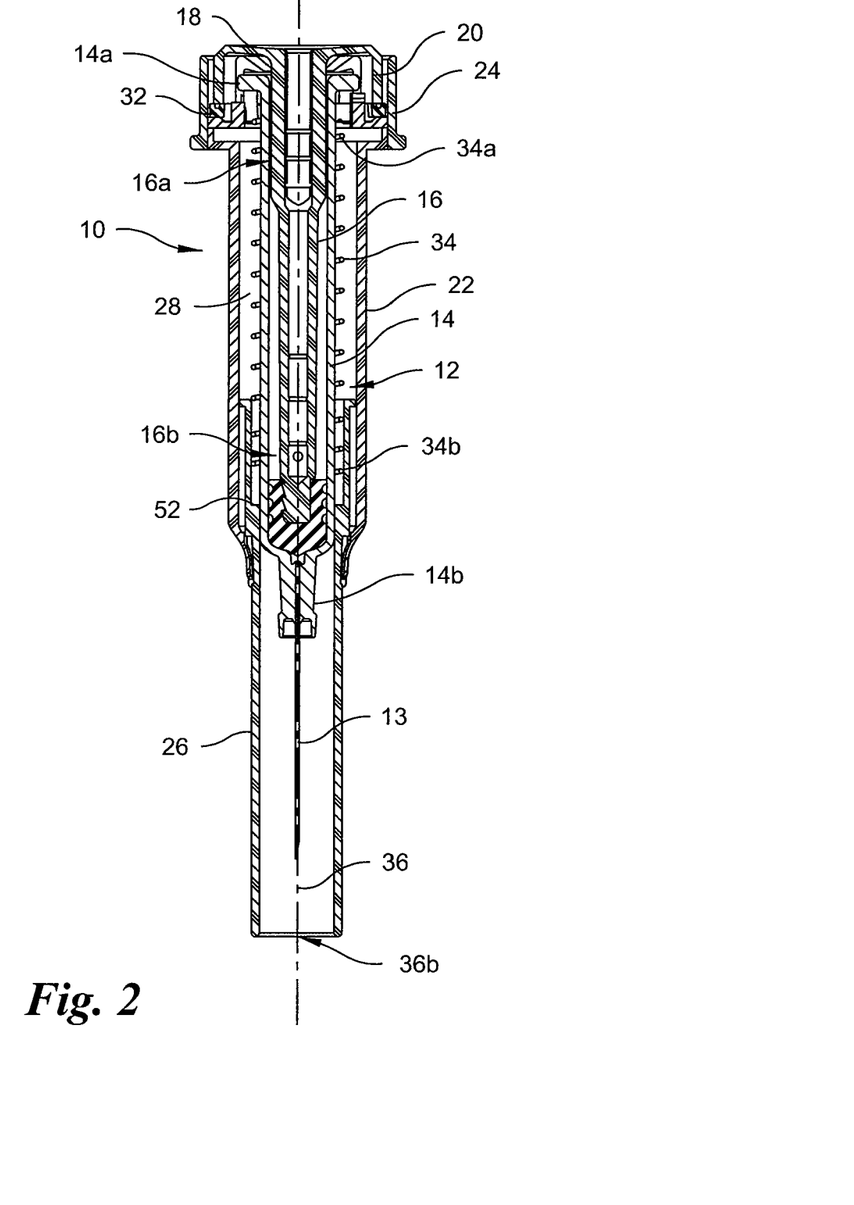
FIG. 2 is a side cross-sectional view of the needle safety shield of FIG. 1, showing the inner tube in the extended position.
Figure 3:
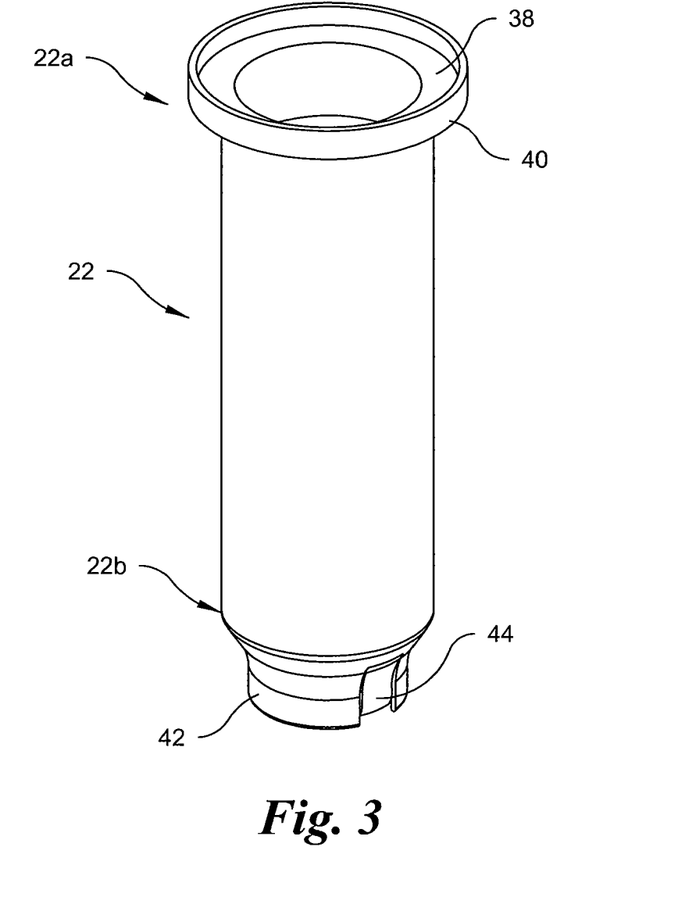
FIG. 3 is a top perspective view of the outer tube of FIG. 1.
Figure 4:
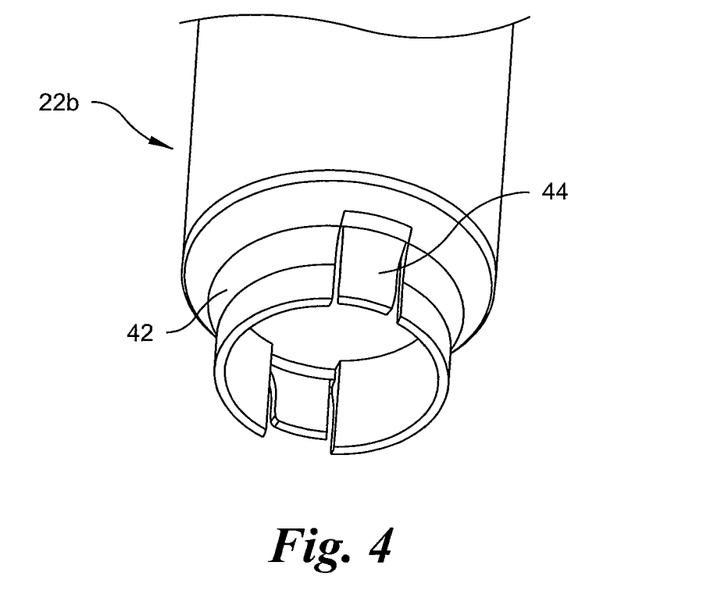
FIG. 4 is a bottom perspective view of a lower portion of the outer tube of FIG. 1.

The drive spring 34 moves the internal tube 26 along the longitudinal axis 36 from a retracted position 36a (see, FIG. 1) to an extended position 36b (see, FIG. 2). More particularly, movement of the plunger rod 16 to engage the activation ring 32 compresses the drive spring 34, moving the activation ring 32 distally, and moving the stop 72 out of engagement with the pin 46, allowing the drive spring 34 to move the second tube 26 into an extended configuration Referring to FIGS. 3-4, the outer tube 22 has a proximal end 22a and a distal end 22b. In some embodiments, the proximal end 22a of the outer tube 22 has a radially outwardly extending flange 38 with an axially extending side wall 40. The distal end 22b of the outer tube 22 has a taper 42 with an axially-extending, radially inwardly-biased finger 44.

Figure 5:
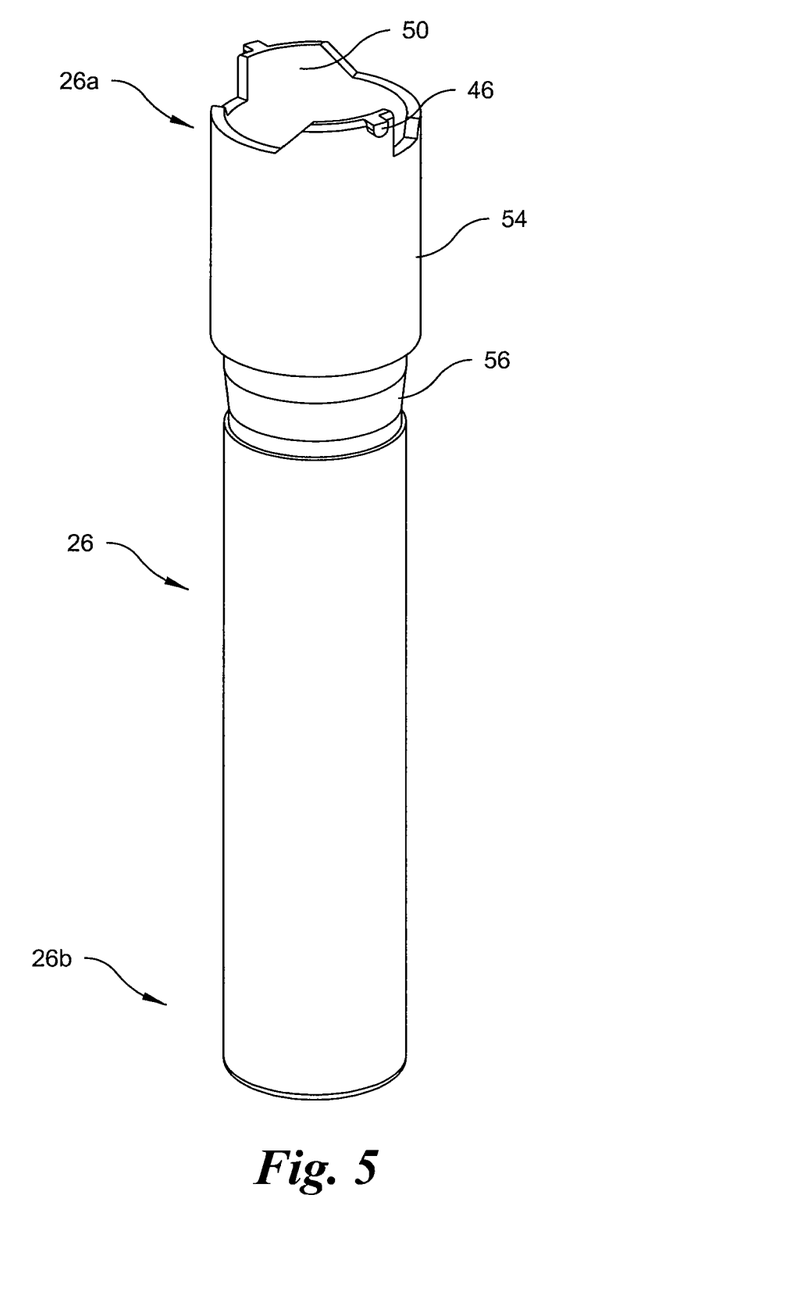
FIG. 5 is a top perspective view of the inner tube of FIG. 1.
Figure 6:
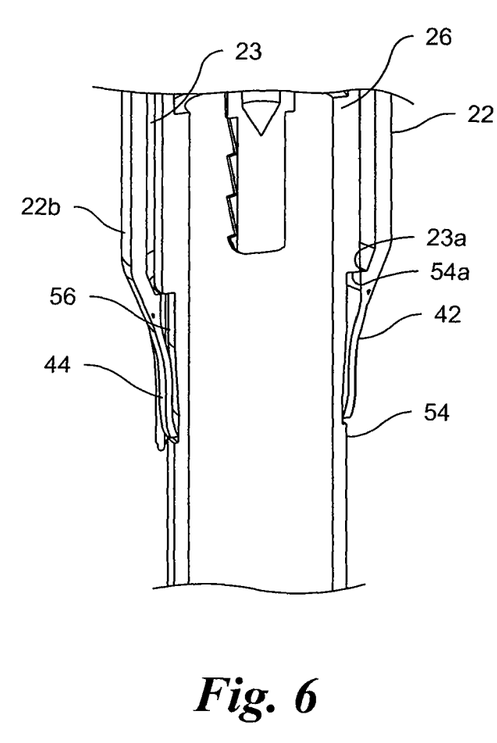
FIG. 6 is side cross sectional view of the mid-portion of the inner tube and the lower portion of the outer tube of FIG. 1 showing the fingers of the outer tube in the locked position.

Referring to FIGS. 5-6, the inner tube 26 has a proximal end 26a and a distal end 26b. In some embodiments, the pin 46 extends radially outwardly from the proximal end 26a of the inner tube 26. The inner tube 26 is slideable axially between a retracted position 36a in which the pin 46 is releasably retained by the activation-ring stop 72 described below and an extended position 36b in which the inner-tube pin 46 is released by the activation-ring stop 72 and the inner tube 26 projects beyond the distal end 14b of the syringe barrel 14.

The inner tube 26 has an interior wall 50 with a circumferential step 52 spaced from the proximal end 26a of the inner tube 26. As shown in FIGS. 1-2 and 10A-10C, the step 52 operatively couples the inner tube 26 to the thrust spring 34 by providing a bearing surface for the distal end 34b of the spring 34.

Referring to FIGS. 2, 5 and 6, the outer surface 54 of the inner tube 26 has a detent 56 in register with the finger 44 of the outer tube 22 when the inner tube 26 is in the extended position 36b. The detent 56 is configured to releasably receive the finger 44. The distal end 22b of the outer tube 22 has an inner surface 23 with a radially inwardly extending shoulder 23a having an inner diameter less than an outer diameter of an opposing shoulder 54a extending radially outwardly from an outer surface 54 of the inner tube 26. The radially inwardly extending shoulder 23a cooperates with the radially outwardly extending opposing shoulder 54a to limit the axial distance the inner tube may move.

Referring to FIGS. 1, 2, 7 and 9, the coupling ring 24 has an axially extending interior wall 58 with a proximal end 58a and a distal end 58b. The coupling ring 24 is configured to receive therein the rim 20 of the actuator head 18. In some embodiments, the outer tube 22 is connected to the coupling ring 24 by a compression fit between the axially extending side wall 40 of the flange 38 of the outer tube 22 and the distal end 58b of the axially extending interior wall 58 of the coupling ring 24. An annular ring 60 spaced from the distal end 58b extends radially inwardly from the interior wall 58. A radially inwardly extending seat 62 is supported by the annular ring 60. The seat 62 supports the proximal end 14a of the syringe barrel 14. A radially inwardly extending barrel latch 64 is supported by the annular ring 60. The barrel latch 64 secures the syringe barrel 14 to the seat 62.

Figure 7:
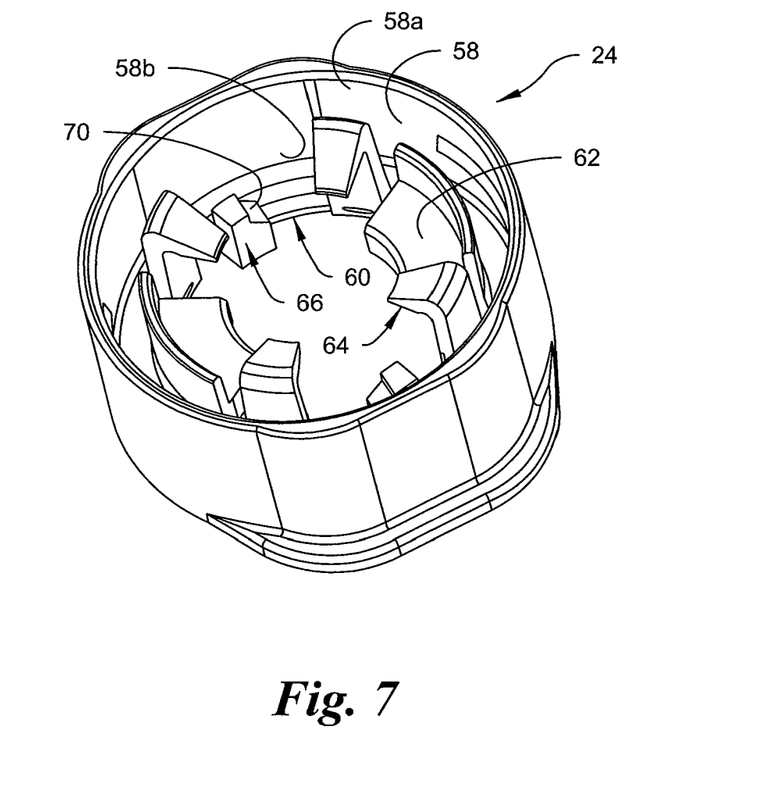
FIG. 7 is a top perspective view of the coupling ring of FIG. 1.

The coupling ring 24 has an inner-tube support 66 extending radially inwardly from the annular ring 60. In some embodiments, the support 66 has an inclined surface 70 extending radially and axially. The inclined surface 70 forms part of a latch 48 releasably retaining the inner tube 26 in the retracted position 36a as further described below.

Referring to FIGS. 1, 2, 8, 9 and 10A, the activation ring 32 comprises a radially inwardly-extending stop 72 movable relative to the support 66. The inner-tube pin 46 is releasably retained on the support 66 by the stop 72. Preferably, the stop 72 is adjacent to and movable axially relative to the support 66. In some embodiments, the support 66 and the stop 72 form the releasable latch 48 (see, FIG. 10A).

Figure 8:
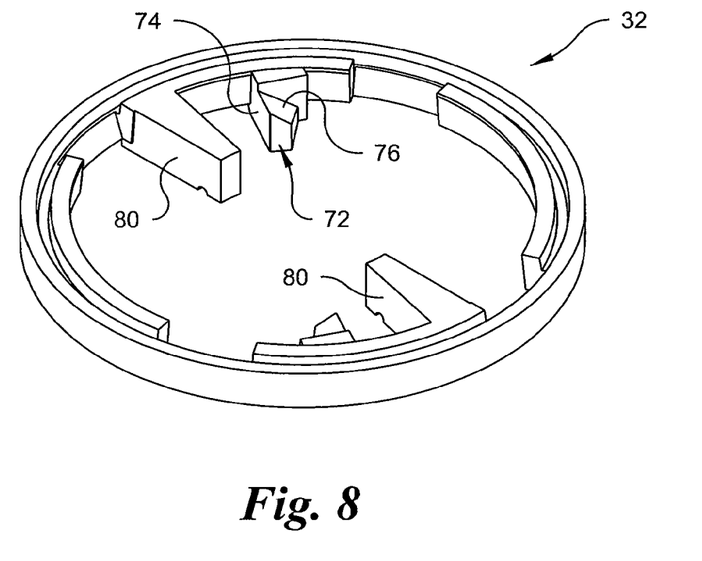
FIG. 8 is a top perspective view of the actuation ring of FIG. 1.
Figure 9:
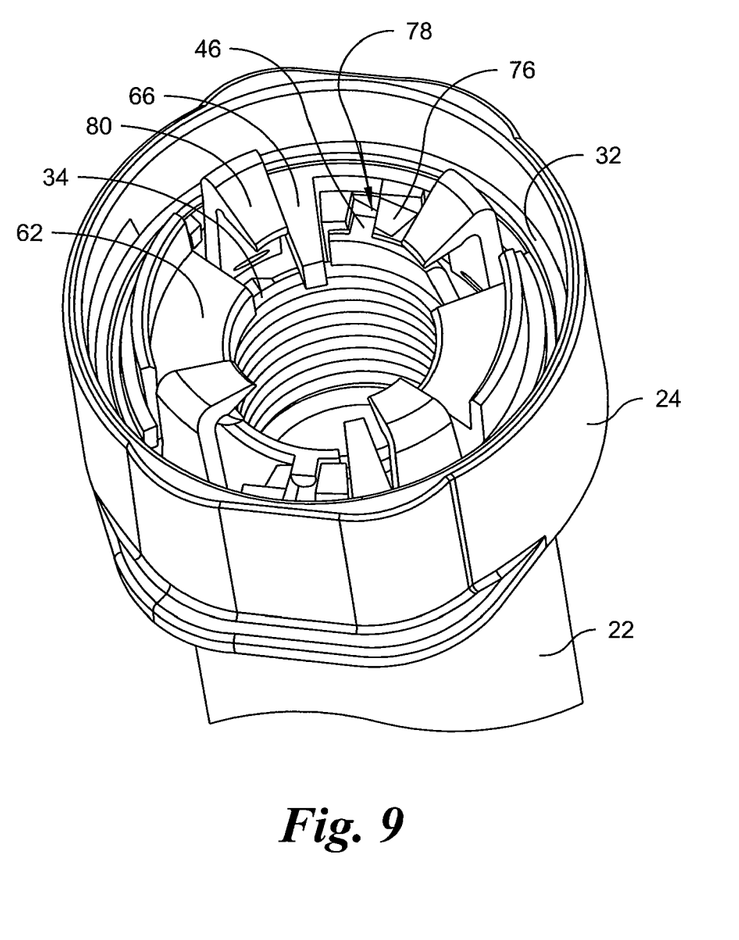
FIG. 9 is a top perspective view of an upper portion of the needle safety shield of FIG. 1 with the pharmaceutical syringe removed.

The stop 72 may have a first surface 74 extending radially and axially and a second surface 76 also extending radially and axially. The first surface 74 may be in sliding contact with the inclined surface 70 of the support 66 of the coupling ring 24. Alternatively, the first surface 74 may be spaced apart from the inclined surface 70. In some embodiments, the second surface 76 may be inclined with respect to the first surface 74 or may have a curvature.

In some embodiments, the releasable latch 48 has a catch 78 (see, FIG. 10A) formed by the inclined surface 70 of the support 66 and the first surface 74 of the stop 72. The inner-tube pin 46 may be releasably retained in the catch 78 when the inner tube 26 is in the retracted position 36a. The inclined surface 70 and the second surface 76 may form an inclined plane along which the inner-tube latch pin 46 slides when the rim 20 of the actuator head 18 axially displaces the activation ring 32. (See FIGS. 10B and 10C). In some embodiments, the inner tube 26 may rotate when the inner-tube pin 46 is released from the stop 72.

Referring to FIGS. 1, 2, 8 and 9, the thrust spring 34 has a proximal end 34a bearing against the activation ring 32 and a distal end 34b bearing against the inner tube 26. A compressive force is applied to the actuation ring 32 by the thrust spring 34 when the inner tube 26 is in the retracted position 36a. The thrust spring 34 moves the inner tube 26 from the retracted position 36a to the extended position 36b when the rim 20 of the actuator head 18 axially displaces the activation ring 32 releasing the inner-tube latch pin 46 from the inner-tube latch 48.

In some embodiments, the thrust spring 34 is in the inner tube 26. The activation ring 32 has a radially inwardly-extending spring support 80. The proximal end 34a of the thrust spring 34 bears against the spring support 80 and the distal end 34b of the thrust spring 34 bears against the step 52 in the interior wall 50 of the inner tube 26.

The safety shield 10 and syringe 12 are used in combination. In an initial state shown in FIGS. 1, 7 and 10A, the proximal end 14a of the barrel 14 of the syringe 12 is supported by the seat 62 of the coupling ring 24 and is secured in place by the barrel latch 64. The inner tube 26 is held in the retracted position 36a by the inner-tube pin 46 releasably retained in the catch 78 formed by the inclined surface 70 of the support 66 of the coupling ring 24 and the first surface 74 of the stop 72 of the activation ring 32 which, in turn, is held snug against the proximal end 14a of the syringe barrel 14 by a force applied to the spring support 80 of the activation ring 32 by a compressed thrust spring 34. The rim 20 of the actuator head 18 of the piston rod 16 is spaced from the actuation ring 32.

Figure 10A:
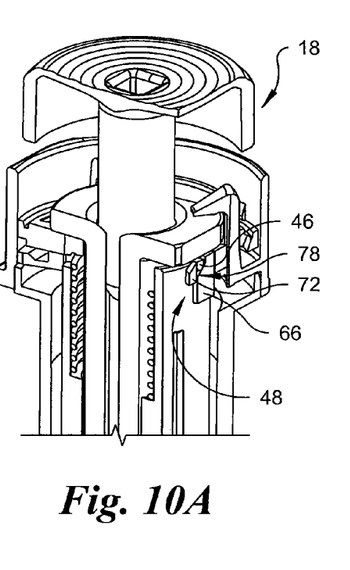
FIG. 10A-10C is a sequence of top perspective views in partial cross-section of the upper portion of the needle safety shield of FIG. 1 showing the progressive axial displacement of the piston rod and the release of the inner-tube pin from the releasable latch.
Figure 10B:
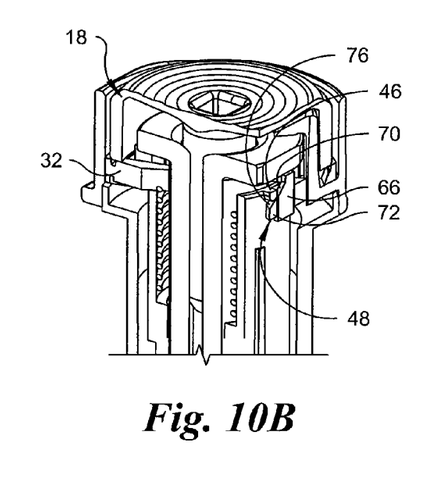

Referring to FIG. 10B, in a second state, the actuator head 18 of the piston rod 16 has been depressed a sufficient axial distance to cause the rim 20 of the actuator head 18 to axially displace the actuation ring 32. The axial displacement of the actuation ring 32, in turn, releases the catch 78, freeing the inner-tube pin 46 from the latch 48, by forming an inclined plane comprising the inclined surface 70 of the support 66 and the fourth surface 76 of the stop 72.

Figure 10C:
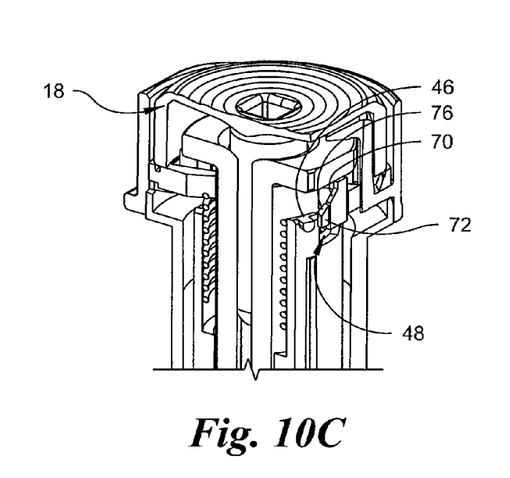

Referring to FIG. 10C, in a third state, under the force applied by the compressed thrust spring 34 to the circumferential step 52 in the interior wall 50 of the inner tube 26, the inner-tube latch pin 46 is driven down and off the inclined plane as the inner tube 26 rotates until the inner-tube pin 46 has passed the stop 72 and is moved axially toward the extended position 36b shown in FIG. 2.

Because the inner-tube pin 46 is releasably retained in the latch 48 and because the latch 48 is "closed" until the actuator head 18 of the piston rod 16 has been depressed a sufficient axial distance to cause the rim 20 of the actuator head 18 to axially displace the actuation ring 32 which, in turn, releases the catch 78, freeing the inner-tube pin 46 from the latch 48, neither shock or vibration prior to assembly of the syringe may unexpectedly cause the protection sheath to move to the extended position. Accordingly, the various embodiments of the invention provide a device which should not activate during transportation of the device or during assembly of the syringe into the device or during transport of the final assembly with the syringe inside.

The foregoing detailed description of the invention has been disclosed with reference to specific embodiments. However, the disclosure is not intended to be exhaustive or to limit the invention to the precise forms disclosed. Those skilled in the art will appreciate that changes could be made to the embodiments described above without departing from the broad inventive concept thereof. Therefore, the disclosure is intended to cover modifications within the spirit and scope of the present invention as defined by the appended claims.

All references, patent applications, and patents mentioned above are incorporated herein by reference in their entirety and are not to be construed as an admission that any of the cited documents constitutes prior art, or as an admission against interest in any manner.

We claim:

1. A needle safety shield for a pharmaceutical syringe having a barrel with a proximal end and a distal end, a piston rod having a distal end slideably received in the barrel, a free proximal end of the piston rod having an actuator head with a rim, the safety shield comprising:
   an outer tube having the syringe barrel therein, a proximal end of the outer tube forming a coupling ring connecting the proximal end of the syringe barrel to the outer tube, the coupling ring configured to receive the rim of the actuator head therein, the coupling ring having a radially inwardly-extending support;
   an activation ring slideably received in the coupling ring, the activation ring comprising a radially inwardly-extending stop movable relative to the support;
   an inner tube in an annular space formed between the syringe barrel and the outer tube, an inner-tube pin extending radially outwardly from a proximal end of the inner tube, the inner tube slideable between a retracted position in which the inner-tube pin is releasably retained on the support by the stop and an extended position in which the inner-tube pin is released by the stop and the inner tube projects beyond the distal end of the syringe barrel; and
   a thrust spring having a proximal end bearing against the activation ring and a distal end bearing against the inner tube, a compressive force being applied to the actuation ring by the thrust spring when the inner tube is in the retracted position,
   wherein the thrust spring moves the inner tube from the retracted position to the extended position when the rim of the actuator head displaces the activation ring releasing the inner-tube pin from the actuation-ring stop.

2. The needle safety shield of claim 1, wherein the radially inwardly-extending stop is movable axially relative to the support.

3. The needle safety shield of claim 1, wherein the radially inwardly-extending support has an inclined surface, the inner-tube pin is releasably retained on the inclined surface by the stop, and the inner tube rotates when the inner-tube pin is released from the stop.

4. The needle safety shield of claim 1, wherein the thrust spring is in the inner tube.

5. The needle safety shield of claim 1, wherein the inner tube has an interior wall with a circumferential step spaced from the proximal end of the inner tube, the activation ring has a radially inwardly-extending spring support, and the proximal end of the thrust spring bears against the spring support and the distal end of the thrust spring bears against the step in the interior wall of the inner tube.

6. The needle safety shield of claim 1, wherein the coupling ring further comprises:
   an axially extending interior wall;
   an annular ring extending radially inwardly from a distal end of the interior wall;
   a radially inwardly-extending seat supported by the annular ring, the seat supporting the proximal end of the syringe barrel; and
   a radially inwardly-extending barrel latch supported by the annular ring, the barrel latch securing the syringe barrel to the seat.

7. The needle safety shield of claim 1, wherein a distal end of the outer tube has a taper with an axially extending, radially inwardly-biased finger, and the inner tube has an outer surface with a detent in register with the finger when the inner tube is in the extended position, the detent configured to releasably receive the finger.

8. The needle safety shield of claim 1, wherein a distal end of the outer tube has an inner surface with a radially inwardly-extending shoulder having an inner diameter less than an outer diameter of an opposing shoulder extending radially outwardly from an outer surface of the inner tube, the radially inwardly-extending shoulder cooperating with the radially outwardly-extending opposing shoulder to limit the axial distance the inner tube may move.

9. A needle safety shield for a pharmaceutical syringe having a barrel with a proximal end and a distal end, a piston rod having a distal end slideably received in the barrel, a free proximal end of the piston rod having an actuator head with a rim, the safety shield comprising:
   an outer tube having the syringe barrel therein, a proximal end of the outer tube forming a coupling ring connecting the proximal end of the syringe barrel to the outer tube, the coupling ring configured to receive the rim of the actuator head therein, the coupling ring having a radially inwardly-extending support with an inclined surface;
   an activation ring slideably received in the coupling ring, the activation ring comprising a radially inwardly-extending stop movable axially relative to the support;
   an inner tube in an annular space formed between the syringe barrel and the outer tube, an inner-tube pin extending radially outwardly from a proximal end of the inner tube, the inner tube slideable between a retracted position in which the inner-tube pin is releasably retained on the inclined surface of the support by the stop and an extended position in which the inner-tube pin is released by the stop and the inner tube projects beyond the distal end of the syringe barrel; and
   a thrust spring in the inner tube, the thrust spring having a proximal end bearing against the activation ring and a distal end bearing against the inner tube, a compressive force being applied to the actuation ring by the thrust spring when the inner tube is in the retracted position,
   wherein the thrust spring moves the inner tube from the retracted position to the extended position when the rim of the actuator head displaces the activation ring releasing the inner-tube pin from the actuation-ring stop.

10. The needle safety shield of claim 9, wherein a distal end of the outer tube has an inner surface with a radially inwardly-extending shoulder having an inner diameter less than an outer diameter of an opposing shoulder extending radially outwardly from an outer surface of the inner tube, the radially inwardly-extending shoulder cooperating with the radially outwardly-extending opposing shoulder to limit the axial distance the inner tube may move.

11. A needle safety shield for use with a syringe having a barrel, a needle and a plunger rod, comprising:
- a first tube;
- a second tube arranged for sliding movement within the first tube:
- a pin connected to one of the first and second tubes;
- an activation ring having a stop; and
- a drive spring biasing the activation ring in a proximal direction to place the stop in engagement with the pin to retain the first and second tubes in a retracted configuration,
- wherein movement of the plunger rod to engage the activation ring compresses the drive spring, moving the activation ring distally, and moving the stop out of engagement with the pin, allowing the drive spring to move the first and second tubes into an extended configuration.

12. The needle safety shield of claim 11, wherein the pin is connected to the second tube.

13. The needle safety shield of claim 12, further comprising a coupling ring connected to the first tube and having a support.

14. The needle safety shield of claim 13, wherein in the retracted configuration the support and stop form a pocket in which the pin is received.

15. The needle safety shield of claim 14, wherein the pocket is formed by an inclined surface on the support extending radially and at an angle to an axis of the first and second tubes, and a first surface on the stop extending radially and parallel to the axis.

* * * * *